US006374829B1

(12) United States Patent
Chapman

(10) Patent No.: US 6,374,829 B1
(45) Date of Patent: Apr. 23, 2002

(54) APPARATUS AND METHOD FOR PROVIDING HEAD, NECK, SPIT, AND BITE PROTECTION DURING AND SUBSEQUENT TO A RESTRAINING HOLD MAINTAINED ON A PERSON

(75) Inventor: Bruce Chapman, Gardiner, NY (US)

(73) Assignee: Handle With Care, Inc., Gardiner, NY (US)

(*) Notice: Subject to any disclaimer, the term of this patent is extended or adjusted under 35 U.S.C. 154(b) by 0 days.

(21) Appl. No.: 09/576,080

(22) Filed: May 20, 2000

(51) Int. Cl.[7] ................................................ A61F 11/00
(52) U.S. Cl. ............... 128/857; 128/869; 128/DIG. 23; 602/18
(58) Field of Search ................................ 128/845, 846, 128/857, 858, 849, 853, 869, 870, DIG. 20, DIG. 23; 602/17, 18, 19; 5/630, 637

(56) References Cited

U.S. PATENT DOCUMENTS 772,148 A * 10/1904 Hughes ............... 128/DIG. 23
1,795,893 A * 3/1931 Rosett ................. 128/DIG. 20
3,189,917 A * 6/1965 Sims .................... 128/DIG. 23
3,765,412 A * 10/1973 Ommaya ..................... 128/857

* cited by examiner

Primary Examiner—Michael A. Brown
(74) Attorney, Agent, or Firm—Edward Etkin, Esq

(57) ABSTRACT

The inventive apparatus and method of use thereof remedies the problems and dangers associated with applying restraint holds to violent and/or struggling persons and provides protection to such persons from self-inflicted injuries during and after application of restraint holds by law enforcement or medical staff members, as well as protects the staff members from harm that may be inflicted on them by the target person during and after application of restraint holds. The inventive modular protective apparatus advantageously comprises three releasably interconnected components: a base resilient pad for providing moderate cushioning support and protection from abrasion for a person's head during application of a restraint hold, an easily deployable cervical collar that protects and stabilizes the person's neck and prevents neck injuries and head-butting, and a readily deployable face shield that releasably attaches to the cervical collar and that prevents the person from spitting on and/or biting the staff members.

16 Claims, 4 Drawing Sheets

APPARATUS AND METHOD FOR PROVIDING HEAD, NECK, SPIT, AND BITE PROTECTION DURING AND SUBSEQUENT TO A RESTRAINING HOLD MAINTAINED ON A PERSON

BACKGROUND OF THE INVENTION

The present invention is directed to a modular apparatus and method, utilized during application of a restraint hold by a group of persons to a target person, for providing head and neck injury protection to the target person and for providing spit and bite protection from the target person to the group applying the restraint hold and to all other persons coming on contact with the target person after application of the restraining hold.

There are many thousands of human service and law enforcement agencies and facilities that provide care and supervision to aggressive, suicidal, and emotionally disturbed persons (hereinafter commonly referred to as "EDPs"). The staff and officers (hereinafter commonly referred to as "staff members") working in these agencies regularly come into physical contact with the EDPs through the use of physical subduing or restraint holds when the EDP becomes aggressive. An example of an a safe and advantageous physical subduing hold is a Primary Restraint Technique (PRT) disclosed in commonly assigned Patent Application entitled "APPARATUS AND METHOD FOR SAFELY MAINTAINING A RESTRAINING HOLD ON A PERSON" Ser. No. 09/442,709, filed Nov. 18, 1999.

During the process of application of a typical restraint hold, the EDP often responds with a violent struggle that may place the EDP at significant risk of head and/or neck injury. This risk is particularly great during application of prone restraint holds where the EDP may repeatedly slam their head on a hard floor surface or rub their face into carpeted surfaces creating what is commonly referred to as a carpet burn. In addition to soft tissue injuries resulting in bruises, such violent behavior may result in cervical spine damage.

Another set of problems arises when the EDP is successfully restrained by a prone restraint and repositioned by the staff members to be escorted to another location, for example on order to apply a prolonged restraint to the EDP. These problems are also very common when a standing restraint hold is applied to the EDP. The first problem is that while being escorted, the EDP may violently shake their head—behavior that may result in neck and cervical spine damage. In addition, such behavior may pose a danger to the staff members escorting the EDP, as the EDP may attempt to head-butt the staff members. The second problem is that EDPs may attempt to spit at and/or bite the escorting staff members—a behavior that is particularly dangerous if the EDP is a carrier of an infectious disease such as AIDS, Hepatitis, and/or Tuberculosis.

Thus, it would be desirable to provide an apparatus and method to assist staff members in protecting the EDP from self-inflicted injuries during and after application of restraint holds, mechanical restraints and/or handcuffs by the staff members. It would further be desirable to provide an apparatus and method to protect staff members from harm that may be inflicted on them by the EDP during and after application of restraint holds by the staff members.

SUMMARY OF THE INVENTION

The apparatus and method of use thereof of the present invention remedies the problems and dangers associated with applying restraint holds to violent and/or struggling EDPs and provides protection to the EDP from self-inflicted injuries during and after application of restraint holds by the staff members, as well as protects the staff members from harm that may be inflicted on them by the EDP during and after application of restraint holds. In brief summary, the inventive modular apparatus advantageously provides: (1) moderate cushioning support and protection from abrasion for the EDP's head during application of a restraint hold in form of a resilient pad, (2) an easily deployable cervical collar that protects and stabilizes the EDP's neck and prevents neck injuries and head-butting, and (3) a readily deployable face shield that attaches to the cervical collar and that prevents the EDP from spitting on and/or biting the staff members. Furthermore, the inventive apparatus may be readily deployed in any situation that requires application of a cervical collar and/or a spit and bite guard, such as for example during an epileptic seizure experienced by a medical patient.

The inventive protective apparatus comprises three releasably attached modules: (1) a resilient pad, (2) a flexible cervical collar releasably attached to the resilient pad, and (3) a clear face shield that is releasably attached to the resilient pad and the cervical collar. The modules are arranged and attached in such a way as to make the deployment process as simple as possible—the staff members position the EDP such that the EDP's head is placed over the resilient pad and the neck is aligned with the cervical collar. The cervical collar is deployed first by detaching the collar from the pad and wrapping the collar around the EDP's neck. The collar contains a releasable attachment mechanism, such as velcro, that facilitates adjustable application of the collar to the EDP's neck. The pad is then detached from the face shield and then removed from under the EDP's head by a staff member. The face shield is then wrapped around the front portion of the EDP's head and releasably attached to the cervical collar (for example by velcro) thus forming a transparent bite and spit guard.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote corresponding or similar elements throughout the various figures.

DESCRIPTION OF THE PREFERRED EMBODIMENTS

The apparatus and method of use thereof of the present invention remedies the problems and dangers associated with applying restraint holds to violent and/or struggling EDPs and provides a margin of protection to the EDP from self-inflicted injuries during and after application of restraint holds by staff members, as well as protects the staff members from certain forms of harm that may be inflicted on them by the EDP during and after application of restraint holds.

It should be understood that while the present invention refers to Emotionally Disturbed Persons (hereinafter "EDPs") and Staff Members, the inventive techniques and apparatus may be applied in virtually any situation where a first person applies a restraining hold, mechanical restraints and/or handcuffs to another person. Thus, the present invention is applicable in law enforcement, hospitals, mental health care facilities, drug and alcohol rehabilitation centers, etc. In addition, the inventive apparatus may be advantageously deployed in any situation that requires application of a cervical collar and/or a spit and bite guard, such as for example during an epileptic seizure experienced by a medical patient. Moreover, it should be understood that embodiments of the present invention described below and illustrated in FIGS. 1A to 3C are shown by way of example only such that relative sizes of various components, and composition of materials of the inventive apparatus may be varied as a matter of design choice without departing from the spirit of the present invention. Finally, while the inventive apparatus is described in reference to application of a restraint hold, it should be understood that portions of the apparatus may be readily and advantageously deployed in any situations where one or more components of the apparatus may be necessary.

Figure 1A:
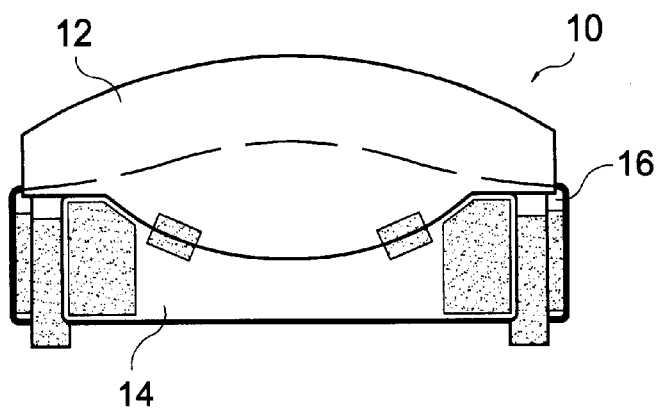
FIG. 1A shows an initial assembled configuration of a protective apparatus of the present invention.

Referring initially to FIG. 1A, an inventive protective apparatus 10 is illustrated in an assembled form. This form facilitates easy storage and transportation of the protective apparatus 10. Because of its flat structure the apparatus 10 may be readily stored in a stacked form or, alternatively, positioned on a wall for rapid deployment. The protective apparatus 10 comprises three separate modules: a resilient cushion pad 12, a cervical collar 14 and a face shield 16.

Figure 1B:
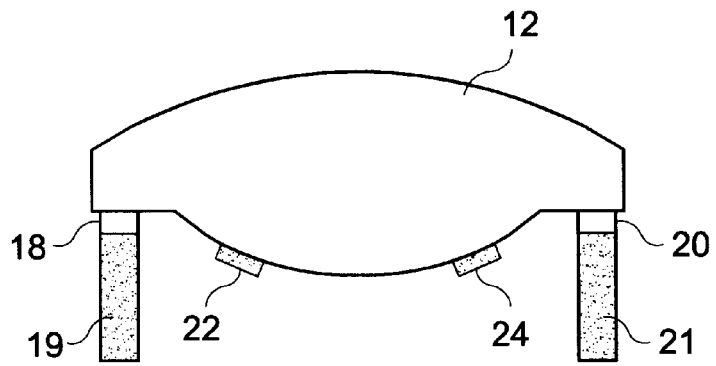
FIG. 1B shows a cushion pad component of the protective apparatus of FIG. 1.

Referring now to FIG. 1B, the resilient cushion pad 12 is a flat, generally rectangular pad preferably composed of a thick, resilient material, such as, for example, dense foam coated with a polyurethane compound. The pad 12 comprises a generally curved upper portion and a lower portion with a generally outwardly curved central section having an outward edge, two straight areas on the left and right sides of the central section having respective corresponding left and right edges. The purpose of the pad 12 is to provide cushioning support and protection from abrasion to the EDP's head when the EDP's head is positioned over the pad during a prone restraint. The specific use of the pad 12 and the protective apparatus 10 is described in greater detail in connection with FIGS. 2A to 2B.

Flexible elongated tabs 18 and 20 are positioned and attached at the respective left and right edges and perpendicular to the respective straight left and right areas on the pad 12 lower portion. The tabs 18 and 20 are preferably of sufficient length to overlap the face shield 16 when the protective apparatus 10 is assembled as shown in FIG. 1. The overlap portions of the tabs 18 and 20 may them be easily lifted to detach the pad 12 from the face shield 16. Each of the tabs 18 and 20 preferably include a first releasable attachment devices 19 and 21, respectively. The first releasable attachment devices 19 and 21 are preferably positioned on undersides of respective tabs 18 and 20. The first releasable attachment devices 19, 21 may be velcro or any other releasable attachment mechanism. Two additional second attachment devices 22, 24 for releasable attachment to the cervical collar 14 are positioned on the outward edge of the central section on respective left and right sections of the outward edge. The second releasable attachment devices 22, 24 may be velcro or any other releasable attachment mechanism.

Figure 1C:
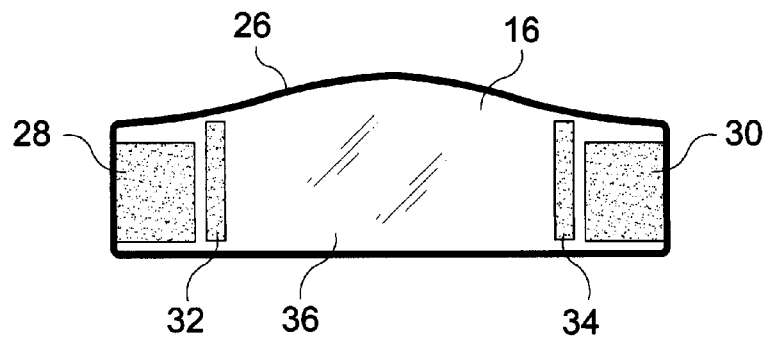
FIG. 1C shows a face shield component of the protective apparatus of FIG. 1.

Referring now to FIG. 1C, the face shield 16 preferably includes a shield 36 composed from a light transparent flexible material such as clear flexible plastic. The shield 36 preferably includes an outer border 26, for example a plastic or rubber sheath along its edge such that the edge is dulled so as not to pose a danger of inflicting cuts on the EDP or staff members. The upper portion of the shield 36 is preferably generally outwardly curved to encompass all of the EDP's face when the face shield 16 is deployed.

The face shield 16 also includes third releasable attachment devices 28, 30 disposed at respective left and right portions of the top surface of the shield 36. The third releasable attachment devices 28, 30 are preferably configured and positioned to receive the tabs 18, 20 such that respective first releasable attachment devices 19, 21 may be placed in releasable contact with the releasable attachment devices 28, 30 when the pad 12 is positioned over and above the face shield 16. The third releasable attachment devices 28, 30 may be velcro or any other releasable attachment mechanism. In addition, the third releasable attachment devices 28, 30 are of sufficient size to at least partially fall under and releasably attach to the cervical collar 14 when it is positioned over the face shield 16. The face shield 16 also includes supplemental fourth releasable attachment devices 32 and 34 positioned respectively proximal to the third releasable attachment devices 28, 30 for providing an additional attachment mechanism to releasably secure the cervical collar 14 to the face shield 16. The fourth releasable attachment devices 32, 34 may be velcro or any other releasable attachment mechanism.

Figure 1D:
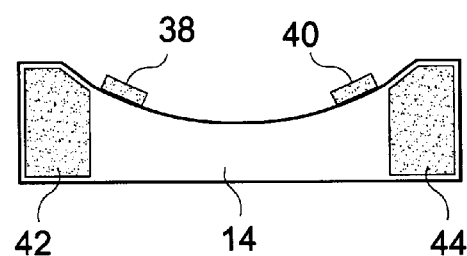
FIG. 1D shows a top view of a cervical collar component of the protective apparatus of FIG. 1.
Figure 1E:
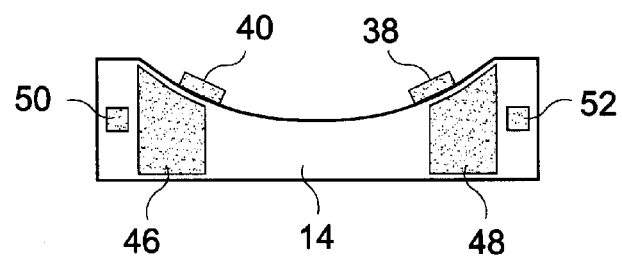
FIG. 1E shows a bottom view of a cervical collar component of the protective apparatus of FIG. 1.
Figure 1F:
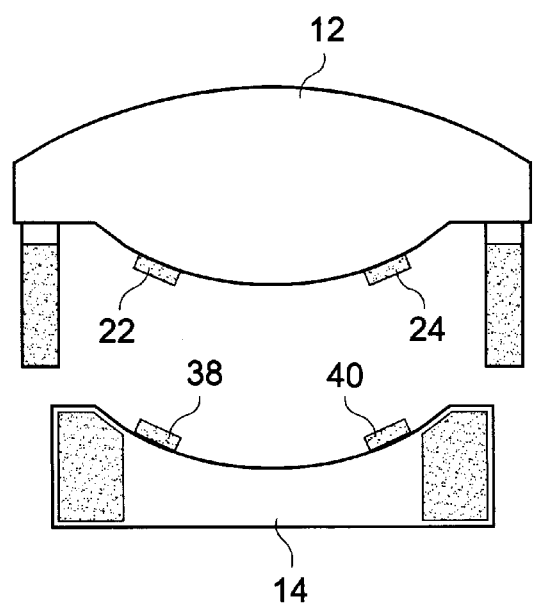
FIG. 1F shows a releasable connection between the cushion pad component of FIG. 1B and the cervical collar component of FIG. 1D.

Referring now to FIGS. 1D and 1E, a top surface of the cervical collar 14, and a bottom surface of the cervical collar 14 are shown, respectively. The cervical collar 14 is preferably composed of a thick, resilient material, such as, for example, dense foam coated with a polyurethane compound. The upper portion of the cervical collar 14 includes a generally inward curved portion having the inner edge configured to receive the outward curved central section of the pad 12, and left and right straight portions on left and right sides of the inward curved portion configured to align with the left and right straight areas of the lower portion of the pad 12. Preferably the length of the collar 14 is configured so that the collar 14 of shorter length than the pad 12 but of sufficient length such that the edges of the collar 12 partially overlap the tabs 18, 20 when the apparatus 10 is in the assembled position. This arrangement is advantageous because it forces the staff members to deploy portions of the apparatus 10 in the correct order—cervical collar 14 first, then detachment of the face shield 16 from the pad 12, and then attachment of the face shield 16 to the cervical collar 14.

Fifth releasable attachment devices 38 and 40 are positioned on the inner edge of the inward curved portion such that they are aligned with the second releasable attachment devices 22, 24, so that when the cervical collar 14 is aligned in the same plane as and under the pad 12, the cervical collar may be releasably attached to the pad 12 when the second releasable attachment devices 22, 24 are placed in releasable contact with fifth releasable attachment devices 38 and 40. The fifth releasable attachment devices 38, 40 may be velcro or any other releasable attachment mechanism.

Sixth releasable attachment devices 42 and 44 are positioned on respective left and right sides on the top surface of the cervical collar 14. Seventh releasable attachment devices 46 and 48 are positioned on respective left and right sides on the bottom surface of the cervical collar 14, but at an offset from the respective left and right edges of the cervical collar 14. Eighth releasable attachment devices 50 and 52 are preferably substantially smaller than the seventh releasable attachment devices 46 and 48, and are positioned on respective left and right sides on the bottom surface of the cervical collar 14, in the respective left and right offset areas to correspond to the fourth releasable attachment devices 32 and 34 on the face shield 16. The smaller size of the devices 50 and 50 facilitates easier detachment of the cervical collar 14 from the face shield 16 and further facilitates deployment of the collar 14 onto the EDP and the removal therefrom.

Figure 2A:
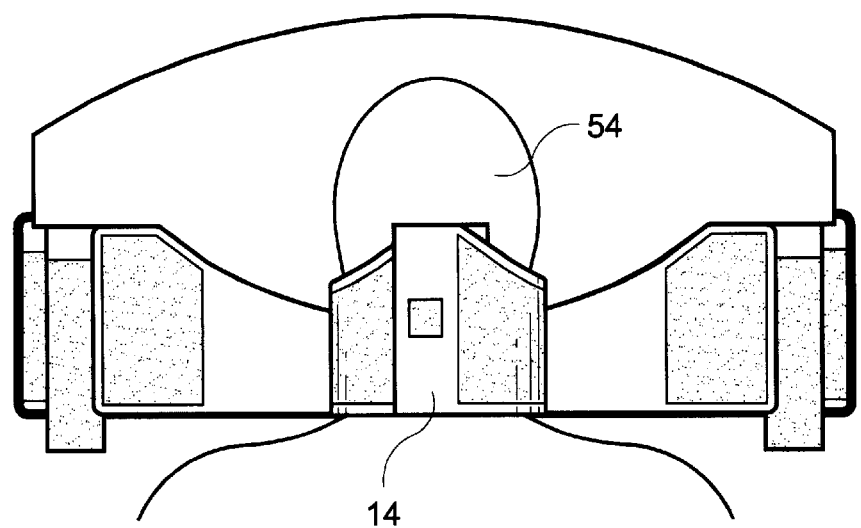
FIG. 2A shows a top view of the cervical collar component of FIG. 1D being deployed on an EDP positioned over the protective apparatus of FIG. 1A.

Each of the devices 42, 44, 46, 48, 50 and 52 is positioned and configured such that when the cervical collar 14 is deployed on the EDP by being folded into a circular shape one of the following arrangements results:

1) the device 42 releasably attaches to devices 46 and 50 if the left portion of the cervical collar overlaps the right portion, or
2) the device 44 releasably attaches to devices 48 and 52 if the right portion of the cervical collar overlaps the left portion (this arrangement is shown in FIG. 2A).

The face shield may be positioned over the EDPs face by releasably attaching the third releasable attachment devices 28, 30 to devices 48 and 46. The sixth, seventh, and eighth attachment devices 42 and 44, 46 and 48, 50 and 52, respectively, may be velcro or any other releasable attachment mechanism.

It should be understood that when various sets of attachment devices are described in reference of being in releasable contact with one another, if such devices are velcro then one of the sets of attachment devices will be hook velcro, while the other set of the attachment devices is loop velcro as a matter of design choice. For example, referring to FIG. 1F, if second releasable attachment devices 22, 24 are hook velcro while the corresponding fifth releasable attachment devices 38 and 40 are loop velcro, and vice versa. Preferably, if the releasable attachment devices are velcro, the actual devices likely to come in contact with the EDP are loop velcro to prevent abrasions more likely to be caused by hook velcro.

Figure 2B:
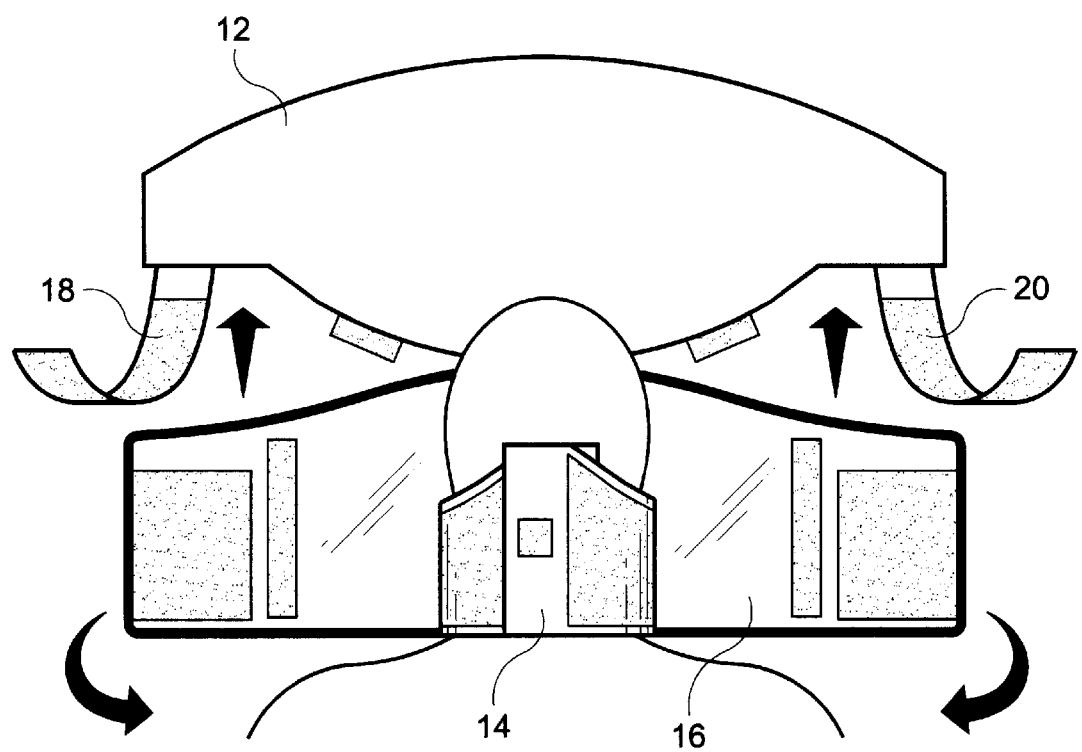
FIG. 2B shows a top view of the face shield component of FIG. 1C being deployed on an EDP after deployment of the cervical collar component as shown in FIG. 2A.

Referring to FIGS. 2A and 2B, the deployment of the various portions of the inventive protective apparatus 10 are shown. First, the EDP 54 is placed into a prone restraint by the staff member(s), and the protective apparatus 10 is positioned by another staff member such that the EDP's head is positioned over the pad 12 and the EDP's neck is aligned with the cervical collar 14. The pad 12, in conjunction with manual stabilization by a staff member, prevents the EDP from slamming their head against a hard floor surface by cushioning any such impacts. The cervical collar 14 is then detached from the pad 12 and the face shield 16 and wrapped around the EDP's neck, with either the left portion of the collar 14 overlapping the right or vice versa. At this point the EDPs neck is secured by the collar 14 which retards forward, back and side to side movement of the EDP's head. This prevents the EDP from moving their head in a manner dangerous to the EDP and to the staff members and prevents head-butting by the EDP after the prone restraint is lifted and the EDP is escorted to another area.

Figure 3A:
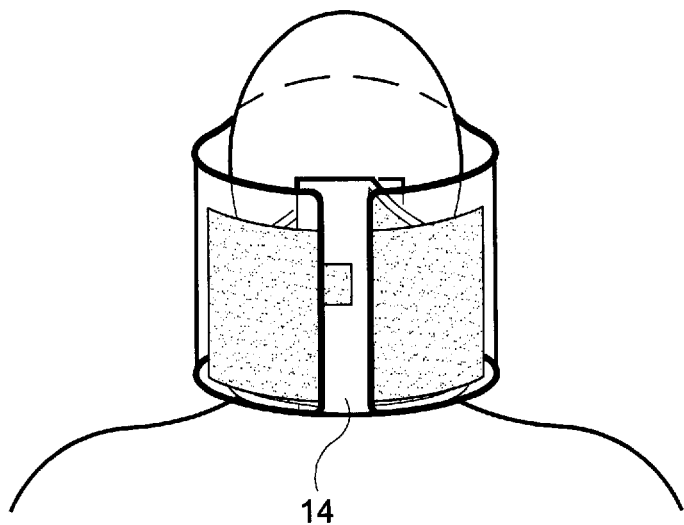
FIG. 3A shows a back view of the cervical collar and face shield components deployed on an EDP in accordance with the present invention.
Figure 3B:
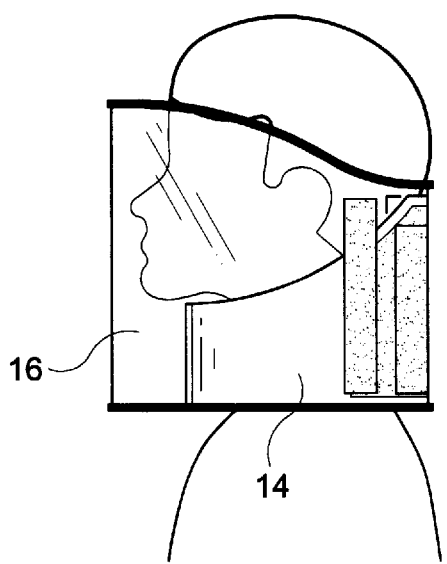
FIG. 3B shows a top view of the deployed cervical collar and face shield components.
Figure 3C:
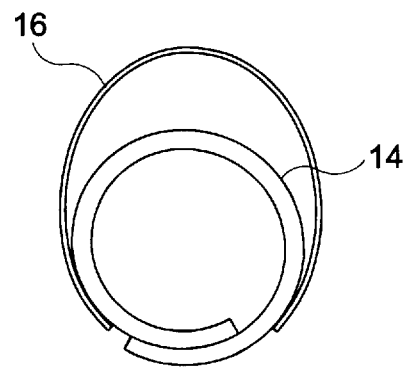

The tabs 18 and 20 are then lifted from the face shield 16 attachment devices 28 and 30 respectively and the pad 12 is removed by a staff member while the face shield is folded around the patient's face such that the respective left and right sides of the shield 16 are attached to the left and right sides of the collar 14 via the third releasable attachment devices 28, 30 being in releasable contact with the seventh releasable attachment devices 48 and 46. The EDP may then be lifted by the staff members from the prone restraint position and escorted, with the face shield 16 protecting the staff members from spitting and/or biting attacks by the EDP. Referring to FIGS. 3A–3C various views of the cervical collar 14 and face shield 16 deployed on an EDP are shown.

Of course the cervical collar 14 and face shield 16 components of the apparatus 10 do not need to be deployed only during a prone restraint of the EDP. The staff members may readily detach the cervical collar 14 and the face shield 16 and use one or both of them in any situation where an EDP's head should be immobilized and/or spit and bite protection is necessary, for example when police transport a detainee (i.e. EDP) in handcuffs.

Thus, while there have shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

I claim:

1. A protective apparatus, utilized during application of a restraint hold by a group of persons to a target person, for providing head and neck injury protection to the target person and for providing spit and bite protection from the target person to the group applying the restraint hold and to all other persons coming on contact with the target person after application of the restraining hold, said apparatus comprising:

a resilient pad of sufficient size to provide substantial support for the target person's head and configured to limit impact and abrasion damage sustained to the target person's head when the target person's head is positioned over said resilient pad during the restraint hold;

a flexible cervical collar having a first side and a second side and comprising first releasable adjustable closing means disposed thereon for securing said collar around the target person's neck when the target person is positioned over the protective apparatus during the restraint hold, wherein said collar is deployed from an open generally flat mode to a circular mode enclosing the target person's neck, such that said cervical collar provides bracing neck support and limits movement of the target person's head during and after the restraint hold;

a flexible substantially transparent face shield having a first end and a second end and comprising releasable adjustable attachment means disposed thereon for:
removably securing said face shield to an underside of said cervical collar when said cervical collar is in said open flat mode, and
removably and adjustably securing said face shield to said cervical collar when said cervical collar is secured around the target person's neck, such that said face shield encloses the target person's face thereby preventing spitting and/or biting attacks by the target person;

first releasable attachment means for releasably connecting said cervical collar to said resilient pad when said cervical collar is in said open flat mode; and second releasable attachment means for releasably connecting said resilient pad to said face shield, wherein said second releasable attachment means is configured to be disengaged prior to removably and adjustably securing said face shield to said cervical collar but after said cervical collar is secured around the target person's neck.

2. The protective apparatus of claim 1, wherein at least one of said resilient pad and said cervical collar are composed of a substantially light and resilient material.

3. The protective apparatus of claim 2, wherein said light resilient material is dense foam coated with a polyurethane compound.

4. The protective apparatus of claim 1, wherein at least one of: first releasable adjustable closing means, releasable adjustable attachment means, first releasable attachment means, and second releasable attachment means are hook and loop.

5. The protective apparatus of claim 4, wherein said hook and loop that is likely to come into contact with the target person's skin is loop material such that abrasion damage to the target person is limited.

6. The protective apparatus of claim 1, wherein said face shield further comprises a protective outer rim disposed around edges thereof for preventing cutting damage by said face shield.

7. The protective apparatus of claim 1, wherein said face shield is composed of clear flexible plastic.

8. The protective apparatus of claim 1, wherein when said cervical collar is in said open flat mode and removably attached to said resilient pad, and wherein said face shield is removably attached to said cervical collar and to said resilient pad, said resilient pad, said cervical collar, and said face shield form a generally flat assembly such that easy storage, transportation and deployment are facilitated.

9. A method, employed during application of a restraint hold by a group of persons to a target person, for utilizing a modular protective apparatus comprising a resilient pad, a cervical collar, and a face shield removably attached to one another to provide head and neck injury protection to the target person and to provide spit and bite protection from the target person to the group applying the restraint hold and to all other persons coming in contact with the target person after application of the restraining hold, said method comprising the steps of:

(a) deploying, on a substantially rigid surface, the resilient pad, the resilient pad being of sufficient size to provide substantial support for the target person's head;

(b) positioning the target person's head over said resilient pad during the restraint hold to limit impact and abrasion damage sustained to the target person's head during application of the restraint hold;

(c) detaching the flexible cervical collar from the resilient pad and from the face shield and removably securing said collar around the target person's neck such that said cervical collar provides bracing neck support and limits movement of the target person's head during and after the restraint hold;

(d) removing the resilient pad from under the target person's head to fully expose the face shield; and (e) removably and adjustably securing said face shield to said cervical collar and positioning said face shield such that said face shield encloses the target person's face thereby preventing spitting and/or biting attacks by the target person.

10. The method of claim 9, wherein at least one of said resilient pad and said cervical collar are composed of a substantially light and resilient material.

11. The method of claim 10, wherein said light resilient material is dense foam coated with a polyurethane compound.

12. The method of claim 9, wherein the resilient pad, said cervical collar and said face shield are removably secured to one another by hook and loop.

13. The method of claim 9, wherein said hook and loop that is likely to come into contact with the target person's skin is loop material such that abrasion damage to the target person is limited.

14. The method of claim 9, wherein the face shield further comprises a protective outer rim disposed around edges thereof for preventing cutting damage by said face shield during and after said step (e).

15. The method of claim 9, wherein said face shield is composed of clear flexible plastic.

16. The method of claim 9, further comprising the steps of:

(f) removing the face shield from the cervical collar and placing the face shield into a generally open flat position;

(g) removing the cervical collar from the target person's neck and placing the cervical collar into a generally open flat position;

(h) removably attaching the resilient pad to the face shield; and (i) removably attaching the cervical collar to the resilient pad and to the face shield such that the resilient pad, the cervical collar, and the face shield form a generally flat assembly thereby facilitating easy storage, transportation and future deployment.

* * * * *